United States Patent [19]
Sandell

[11] Patent Number: 5,780,240
[45] Date of Patent: Jul. 14, 1998

[54] ASSAYS FOR CARTILAGE SYNTHESIS IN OSTEOARTHRITIS BASED ON DETECTION OF TYPE IIA PROCOLLAGEN/PROPEPTIDE

[75] Inventor: Linda J. Sandell, Seattle, Wash.

[73] Assignee: University of Washington, Seattle, Wash.

[21] Appl. No.: 682,412

[22] Filed: Jul. 17, 1996

Related U.S. Application Data

[63] Continuation of Ser. No. 198,962, Feb. 18, 1994, Pat. No. 5,541,066.
[51] Int. Cl.[6] .................. G01N 33/53; G01N 33/567
[52] U.S. Cl. .................. 435/7.1; 435/7.21; 435/7.92
[58] Field of Search .................. 435/7.1, 7.21, 435/7.92

[56] References Cited

PUBLICATIONS

Ryan et al., J. Biol. Chem. 265:10334, 1990.
Shinmei et al., Osteoarthritis and Cartilage 1:128, 1993.

*Primary Examiner*—Stephanie W. Zitomer
*Attorney, Agent, or Firm*—Virginia H. Meyer, Esq.

[57] ABSTRACT

Assays for determining cartilage synthesis associated with osteoarthritis are presented. The assays are based on detection of type IIA procollagen or propeptide, or type IIA mRNA in a tissue or fluid sample from a non-neonatal individual being tested. Since type IIA procollagen is not found in normal non-neonatal individuals, type IIA procollagen and the mRNA which encodes it are unique markers for osteoarthritis which exhibits neonatal like cartilage synthesis as part of the disease syndrome.

11 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: preRNA ( x i ) SEQUENCE DESCRIPTION: SEQ ID NO:1:

TGCCAGCCTC CTGGACATCC TGGC 24

( 2 ) INFORMATION FOR SEQ ID NO:2:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: preRNA ( x i ) SEQUENCE DESCRIPTION: SEQ ID NO:2:

CTCCTGGTTG CCGGACATCC TGGC 24

( 2 ) INFORMATION FOR SEQ ID NO:3:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:3:

Cys Glu Asp Val Lys Asp
1             5

( 2 ) INFORMATION FOR SEQ ID NO:4:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:4:

Cys Pro Thr Asp Leu Ala Thr Ala Ser Gly
1             5                       10

ASSAYS FOR CARTILAGE SYNTHESIS IN OSTEOARTHRITIS BASED ON DETECTION OF TYPE IIA PROCOLLAGEN/PROPEPTIDE

RELATED APPLICATION

This application is a divisional of U.S. application Ser. No. 08/198,962 filed Feb. 18, 1994, which issued as U.S. Pat. No. 5,541,066 on Jul. 30, 1996.

GOVERNMENT RIGHTS

This invention was made with government support under NIH Grant R07 36994 and support from the Department of Veterans Affairs. The government has certain rights in the invention.

FIELD OF THE INVENTION

The present invention relates to assays for detection of cartilage synthesis in osteoarthritis based on detection of type IIA procollagen and/or propeptide, and/or type IIA mRNA. The assays of the invention are useful as diagnostic and monitoring aids for osteoarthritis, and/or as aids in determining the effectiveness of osteoarthritic drugs and therapies.

BACKGROUND

Collagen is one of the most abundant animal proteins in nature. It is present in all types of multicellular animals, including humans, where it is estimated to account for about 30% of the total human body protein. Collagen constitutes the fibrillar component of the soft connective tissues (e.g., skin, ligaments, and tendon) and is the major component of the organic matrix of calcified tissues such as bone and dentine. In addition to its structural significance, collagen plays an important role in development and wound healing, and has been implicated in aging and some disease processes.

There are several genetically distinct types of collagen, which are referred to as types I, II, III, and so forth. Type II collagen is the major collagen of cartilage. It is synthesized by chondrocytes as a procollagen molecule with noncollagenous aminopropeptide and carboxypeptide extensions. These two extensions are removed by specific peptidases before type II collagen is incorporated into fibrils.

Type II collagen can be expressed in two forms by differential splicing of the primary gene transcript. The two mRNAs either include or exclude an exon (exon 2) encoding the major portion of the amino propeptide. The mRNA including exon 2 is referred to as type IIA mRNA; the mRNA excluding exon 2 is referred to as type IIB. The proteins encoded thereby are referred to as type IIA procollagen and type IIB procollagen, respectively. The peptide encoded by exon 2 is referred to as type IIA propeptide. Ryan, M. C. and Sandell, L. J., (1990) *J. Biol. Chem.* 265:10334. Type IIB mRNA is primarily expressed by chondrocytes, while type IIA is expressed in chondroprogenitor cells. Sandell, L. J., et al., (1991) *J. Cell Biol.* 114:1307.

Osteoarthritis (OA) is characterized by the destruction of articular cartilage. Despite the ultimate degeneration of articular cartilage associated with OA, a striking phenomenon of OA cartilage is an attempt by chondrocytes to repair their matrix. This is characterized by proliferating chondrocyte clones, the development of chondroosteophytes and the synthesis of collagen.

There is a need for cartilage markers that can provide information on collagen metabolism of diseased cartilage. Such markers are useful in estimating the pathological conditions of diseases such as OA. In this regard Shinmei et al ((1993) *Osteoarthritis and Cartilage* 1:128) have suggested that since type II collagen is a unique component of cartilage, the carboxy-terminal type II procollagen peptide (pCOL II-C) levels in joint fluids could reflect the synthetic activity of type II chondrocytes in the diseased joint, and thus could be used as a simple marker of type II collagen synthesis in articular cartilage in joint diseases. Unfortunately use of pCOL IIC as a marker for OA associated cartilage synthesis, as suggested by Shinmei et al. ((1993) *Osteoarthritis and Cartilage* 1:128), is not entirely satisfactory since non-diseased chondrocytes synthesize type II collagen, including type IIB collagen. Although there is evidence for increased synthesis of type II collagen at sites of pathological degradation of cartilage, use of pCOL IIC as a marker does not distinguish whether the increased synthesis is "normal" or associated with a disease state. Use of pCOL IIC also does not distinguish between type IIA or type IIB propeptide, since type IIA and IIB propeptides share the same carboxy-terminal ends.

There is a need for assays which can distinguish type IIA and type IIB procollagens, since only type IIA procollagen is unique to disease states such as osteoarthritis.

SUMMARY

The present invention is directed to assays for identifying type IIA mRNA and/or type IIA procollagen/propeptide in samples from non-embryonic individuals being tested for osteoarthritis. The assays are based on the surprising discovery that chondrocytes from OA cartilage (i.e., chondrocytes from cartilage taken from human patients with OA) strongly express type IIA procollagen mRNA in addition to type IIB procollagen mRNA. This is a very surprising result since usually type IIA procollagen is only expressed during embryogenesis, and is not a normal component of mature cartilage. Consequently, type IIA procollagen and type IIA propeptide, and type IIA mRNA are unique and useful markers for OA. Accordingly the invention teaches detection of type IIA mRNA or type IIA procollagen and/or propeptide in a sample from a non-embryonic human as a means of showing cartilage synthesis associated with osteoarthritis.

The presence of type IIA mRNA or type IIA procollagen and/or propeptide in the sample being tested can be detected by any means known to the art. For example, type IIA mRNA can be detected using in situ hybridization to riboprobes, or the type IIA mRNA can be identifies using northern blot techniques. The mRNA can also be isolated and identified using nuclease protection analysis techniques. Type IIA procollagen and/or propeptide can be identified in fluid samples using immunological techniques, or in tissue samples using immunohistochemical techniques. Alternatively, the peptides can be isolated, and sequenced.

More particularly, in one aspect the present invention comprises as assay for detecting type IIA mRNA or type IIA protein encoded thereby (i.e., protein encoded by exon 2 of the human pro-$\alpha$1(II) gene, e.g., type IIA procollagen or type IIA propeptide) in joint tissue or fluid samples from non-embryonic individuals being tested. According to this aspect of the invention, a sample of joint tissue or fluid (e.g., serum, synovial fluid, or urine) is contacted with a molecule or agent able to identify the presence of type IIA mRNA or type IIA procollagen or proprotein in the sample. (The body fluid may be used as is or purified prior to the contacting step. Purification may be accomplished using techniques known in the art, e.g., chromatography, dialysis, etc.) If there is a reaction, it will be known that the sample contains type IIA mRNA and/or procollagen and/or proprotein. Since type IIA protein or mRNA are not present in non-disease states, the information regarding the presence or absence of type IIA mRNA or procollagen and/or proprotein in the sample can then be used by the physician or skilled worker as needed, e.g., as a diagnostic and monitoring aid for OA, and/or as an aid in determining the effectiveness of osteoarthritic drugs and therapies.

Alternatively, since the nucleotide sequence of the human COL2A1 gene is known, as is the sequence of the protein encoded thereby, the mRNA or protein in the sample suspected of being type IIA can be sequenced to determine if type IIA is present.

According to the invention, in preferred form, the sample is fluid (e.g., serum, synovial fluid, or urine) from an adult human individual being tested, and the identifying agent(s) is one or more antibodies (polyclonal or monoclonal) which react with at least one determinant on the type IIA peptide (i.e., the peptide domain encoded by exon 2 of the COL2A1 gene, e.g., type IIA propeptide or type IIA procollagen). Alternatively, the presence of type IIA mRNA in joint tissue from adult individuals being tested can be determined by in situ hybridization to mRNA, while type IIA procollagen or propeptide in tissue samples can be identified using known methods such as immunohistochemical techniques. Samples of cartilage for the assays can be obtained by arthroscopy of the joint or upon surgery.

These and other features, aspects and advantages of the present invention will become better understood with reference to the following description, examples and appended claims.

DESCRIPTION

Osteoarthritis is a degenerative disease of the articulating cartilages of the joints. In its early stages it is largely non-inflammatory. As a result, it is difficult to diagnose in its early stages. In normal adults, there is no cartilage synthesis which involves type IIA mRNA or peptides encoded thereby. This makes type IIA mRNA and type IIA propeptide and type IIA procollagen unique markers for osteoarthritis.

The assays of the invention can be used to detect early incidence of osteoarthritis, as well as more advanced states, to monitor the disease in patients, and as means of monitoring the effects of drugs or other therapies. In the long term, assays of the invention which use body fluids (e.g., serum or urine) could be used as routine screening methods for identifying those individuals which show signs of osteoarthritis (as judged by the presence of type IIA procollagen or propeptide in the body fluid). Such individuals could be targeted for early preventive therapies. For individuals with more advanced stages of the disease, the assays of the invention can be used to monitor the state of the disease, and to evaluate responses to therapy.

In the examples that follow, probes specific for type IIA and type IIB collagen are given. The probes can be used in in situ hybridization assays to determine the presence of type IIA mRNA in cartilage from individual(s) being tested. According to this aspect of the invention, a non-embryonic human articular cartilage sample is contacted with at least one RNA probe which hybridizes to mRNA encoded by exon 2 of the human pro-α-1(II) gene, using standard in situ hybridization techniques. Type IIA mRNA in the sample is determined based on the presence or absence of a hybridization reaction. It is known that type IIA and type IIB procollagens are present in proportion to the amount of mRNA, so analysis of mRNA levels is indicative of the presence of type IIA and type IIB procollagens.

Alternatively, known histochemical techniques can be used to determine the presence of type IIA procollagen in human articular cartilage. According to this aspect of the invention, a non-embryonic human articular tissue sample is contacted with at least one antibody to at least one antigenic determinant on the amino peptide encoded by exon 2 of the human pro-α-(II) gene. The presence of type IIA procollagen in the sample is determined from the presence or absence of an antibody-antigen complex.

Also according to the teaching of the invention, known immunological techniques can be used to prepare antibody (polyclonal or monoclonal) that reacts with antigenic determinants on protein encoded by exon 2 of the human pro-α-1(II) gene. Example VII discloses preferred antigenic regions from human type IIA procollagen which can be used to generate peptide antigens for use in immunoassays according to the invention. For polyclonal antibodies, the immunized animal will preferably be a rabbit. Monoclonal antibodies can also be prepared, using techniques known in the art. In this aspect of the invention, a sample, either tissue or fluid from a non-embryonic individual being tested, is contacted with antibody to at least one antigenic determinant on type IIA procollagen. The presence of type IIA procollagen or type IIA propeptide in the sample is then determined based on the presence or absence of antibody-antigen complex. This aspect of the invention is further illustrated in Example VIII.

Other aspects of the invention are illustrated in the examples that follow.

EXAMPLES

Example I

In Situ Hybridization

Tissue for in situ hybridization assay is frozen, preferably in O.C.T. compound (Miles Laboratories Inc., Elkhart, Ill.) and sectioned with a cryostat, or fixed in 4% paraformaldehyde, embedded in Epon, and sectioned on a microtome. For in situ hybridization, frozen sections are preferably used with in situ hybridization procedures described by Lewis et al (1985) *Peptides* 2:75–87. In sum, slides with a section of tissue are warmed to room temperature. Sections are postfixed in 4% paraformaldaldehyde, treated with acetic anhydride (0.25% in 0.1 M triethanolamine), dehydrated, delipidated, and air dried. A radiolabed oligonucleotide probe is added to hybridization buffer containing 50% deionized formamide, 10% dextran sulfate, 300 mM NaCl, 10 mM Tris, 1 mM EDTA, 1X Denhardt's (0.02% each of BSA, Ficoll, and polyvinylpyrollidone), 0.5 mg yeast tRNA/ml, and 10 mM dithiothreitol. A 45-μl aliquot (containing 2.5 pmol of probe/ ml) is applied to the slide. Specific activity estimates may typically range from 1.0 to $1.2 \times 10^7$ cpm/pmol. Sections are coverslipped and slides are incubated overnight in moist chambers at 37° C. After the overnight incubation, coverslips are removed and sections washed four times in 1 X standard saline citrate (1X SSC=150 mM NaCl, 15 mM sodium citrate) for 15 min at 50° C. When desired, stringency can be increased by elevating wash temperatures. Slides are washed twice for 1 h at room temperature. The sections are dehydrated through a graded series of alcohols containing 300 mM ammonium acetate and exposed, preferably using Hyperfilem BMax (Amersham Corp.), for 3 days. Slides are dipped in NTB 2 emulsion (Eastmen Kodak Co., Rochester, N.Y.), diluted 1:1 with 600 mM ammonium acetate and exposed for 8–12 days. The emulsion is developed, preferably in D-19 (Eastman Kodak Co.), diluted 1:1 with distilled water at 16° C. Sections are counterstained with cresyl violet acetate and coverslipped. Autoradiographs are analyzed, preferably with the aid of a MCID Image Analysis System (Imaging Research, St. Catherines, Ontario, Canada).

Example II

RNA Probes

Probes specific for type IIA and type IIB collagen have been described (Ryan and Sandell, (1990) *J. Biol. Chem.* 265:10334). In sum, to detect type IIA collagen mRNA in which exons 1 and 2 are contiguous, it is preferable to use a 24-bp oligonucleotide probe (5' TGCCAGCCTCCTGGA-CATCCTGGC 3') corresponding to 12 nucleotides at the 3' end of exon 1 and 12 nucleotides at the 5' end of exon 2. To detect type IIB collagen mRNA from which exon 2 have been removed, thereby connecting exon 1 to exon 3, it is preferable to use a 24-bp probe (5' CTCCTGGTTGCCG-GACATCCTGGC 3') corresponding to 12 nucleotides at the 3' end of exon 1 and 12 nucleotides at the 5' end of exon 3. The oligonucleotide probes are synthesized using known techniques and equipment, purified on acrylamide gel, end labeled with $[\gamma\text{-}^{32}P]ATP$ using T4 DNA polymerase, and hybridizing in 20% formamide solution (20% formamide, 5 X SSPE, 5% SDS). The blots are washed in 2 X SSPE and 1% SDS at 54° C. to eliminate partial hybridization and maintain only hybridization of complete 24-bp oligonucleotides.

Example III

Isolation of Procollagen Containing Cells from Tissue

Procollagen containing cells can be isolated from tissue samples by dispersion with proteases as follows. Articular cartilage slices are incubated at 37° C. with hyaluronidase (1 mg/ml in PBS; preferably bovine testicular from Sigma Chemical Co., St. Louis, Mo., for 10 min, followed by 0.25% trypsin, preferably GIBCO/BRL, Gaithersburg, Md., for 45 min.). The cartilage is then chopped in small fragments and incubated at 37° C. with collagenase 3 mg/ml in serum-free control medium, preferably clostridial peptidase from Worthington Biochemical Corp., Freehold, N.J.) for 24 hours. The dispersed cells are then washed with Ca++ and Mg++ free PBS.

If the cells are to be cultured, they are cultured in Dulbecco's modified Eagle's medium supplemented with 10% FCS with medium changes every 3–4 days. If the procollagens are to be labeled, the cells are preferably labeled 24 h after the last medium change for a further 24 h in serum-free Dulbecco's modified Eagle's medium (5 ml per 10-cm dish) supplemented with 50 µg/ml ascorbate and 50 µg/ml β-aminoproprionitrile fumarate and containing 25 µCi/ml of [$^3$H]proline (>20 Ci/mmol; Amersham Corp., Arlington Heights, Ill.) and 50 µCi/ml of [$^{35}$S]cysteine (1071 Ci/mmol; Amersham Corp.)

Example IV

Isolation of Procollagens from Cells or Body Fluids

Procollagens can be isolated from cells or body fluids as follows. If the cells are cultured, culture medium containing the labeled proteins are preferably adjusted to 5 mM EDTA, and 1 mM N-ethylmaleimide. Procollagens in cells or body fluid are precipitated with ammonium sulfate (e.g., 300 mg/ml, stirred overnight at 4° C.). The precipitate is collected by centrifugation (e.g., 15,000 rpm, 4° C., for 30 min in an SS 34 rotor (Sorvall Instruments, Newton, Conn.) using an RC 5C centrifuge (Sorvall Instruments)). The precipitate is preferably suspended in 0.05 M Tris-HCL, pH 7.5, 0.25 M NaCl, 0.1% Triton X-100.

If the procollagens are to be labeled, the samples may be treated with 0.25% diisopropyl fluorophosphate for 4 h on ice and then dialyzed against the same buffer. Samples are run over a Sepharose-gelatin column to remove fibronectin, and other impurities. Labeled proteins are visualized by fluorography after separation on SDS-PAGE, preferably using Amplify (Amersham Corp.).

Example V

Type IIA Procollagen is Reexpressed in OA

The object of the study in this example was to investigate the capacity of cells to synthesize collagen in OA. In the study in situ hybridization was performed using probes to localize the mRNAs for collagen types I, IIA and total type II in OA samples. A probe for type I collagen mRNA was used since this message is expressed by fibroblasts, bone cells and dedifferentiated chondrocytes. The expression of type IIA procollagen mRNA, which is characteristic of chondroprogenitor cells (*J. Cell Biol.* (1991) 144:1307), was detected using a specific probe to this transcript. In addition a probe was used to detect total type II procollagen mRNA which would hybridize to both alternatively spliced mRNA forms including the type IIB transcript which is expressed by chondrocytes.

Methods

Several representative samples of cartilage and chondroosteophytes were obtained from each of 7 patients undergoing knee replacement at the Veterans Administration Medical Center, Seattle. Five normal cartilage samples were obtained from the Northwest Tissue Center, Seattle, and served as controls. All samples were quick-frozen and cryosectioned. In situ hybridization of types I, II and IIA messages were performed using methods described in *J. Biol. Chem.* (1991) 144:1307, which is incorporated by reference herein. Riboprobes were developed using cDNA sequences to exon 2 (type IIA) and exons 1–3 (type II) of type II collagen inserted into pBllsk(+) vectors (Statagene, La Jolla, Calif.). (Probes specific for type IIA and type IIB collagen are described in Ryan, M. and Sandell, L. (1990) *J. Biol. Chem.* 265:10334, which is incorporated by reference herein). The type II fragment contains mostly sequence from exon 1 and therefore would hybridize to both the type IIA and IIB messages. A 206 bp type I cDNA insert was cloned into the Kpn-HincII site of pGEM4Z (Promega, Madison Wis.). All plasmids were linearized and transcribed in vitro using T3 and T7 (types IIA and II) or T7 and SP6 (type I) RNA polymerases to generate $^{35}$S-labeled antisense and sense transcripts, respectively.

Results

Sections of control cartilage showed normal chondrocytes residing in a uniform matrix. While some chondrocytes in these samples expressed the message for total type II procollagen, no hybridization for the type IIA message was observed (data not shown). In contrast to normal cartilage, samples of OA cartilage exhibited abnormal chondrocyte clones residing in fibrillated and disorganized matrix (data not shown). These chondrocytes strongly expressed IIA mRNA (data not shown). Moreover, the expression of total type II mRNA (type IIA+IIB) was increased in OA cartilage chondrocytes compared to chondrocytes from normal cartilage controls. Sections probed for type I mRNA showed no hybridization of this message in OA or normal cartilage (data not shown). Serial sections of OA cartilage probed with an irrelevant mRNA probe, dopamine transporter, showed no hybridization and served as an additional control.

In samples of chondroosteophytes, two distinct regions were apparent. In one region, hyperplastic fibroblast-like cells were surrounded by a matrix of loose connective tissue. These cells expressed type I mRNA. In the other region, chondrocyte-like cells resided in areas of metachromic staining. These cells expressed type IIA and total type II mRNAs.

Von der Mark, K. et al. ((1992) *Articular Cartilage and Osteoarthritis*, Raven Press, Page 221) have reported synthesis of type II procollagen mRNA in OA. In the present study it is demonstrated that the type IIA procollagen splice form is also expressed by OA chondrocytes and chondrocyte-like cells of chondroosteophytes. This finding is surprising and unique since type IIA mRNA is normally expressed by chondroprogenitor cells, not chondrocytes. These IIA expressing cells do express type I collagen mRNA. These results indicate that OA chondrocytes do not dedifferentiate but favor the repair of cartilage matrix by recapitulating a pattern of developmental expression.

Example VI

Preparation of Antisera to Human Type IIA Procollagen Specific Peptide

Preferably antisera is generated using peptide antigens injected into rabbits. The peptides are selected from the known sequence of human type IIA procollagen-specific peptide. Preferably sequences are selected based on low homology to type I and type III procollagens and potential for antigenicity. Two regions are especially preferable. One region is hydrophilic and has the following sequence: Cys-Glu-Asp-Val-Lys-Asp. The other is hydrophobic and has the following sequence: Cys-Pro-Thr-Asp-Leu-Ala-Thr-Ala-Ser-Gly. These sequences are preferred because when screened for possible homology to other chondrocyte proteins, none were found. The amino acid sequences are preferably synthesized. For immunization, the amino acid sequences are preferably coupled to keyhole lipet hemocyanin (KLH) via the sulfhydryl groups of the amino-terminal cysteine residues. Coupling is preferably accomplished by using maleimide activated KLH (Imject kit, Pierce, Rockford, Ill.). Most preferably, antibodies are generated in New Zealand rabbits. After each boost, serum levels of specific antibody to the uncoupled peptide is determined by ELISA.

Example VII

Identification of Type IIA Procollagen Using Immunoassay

Using the method disclosed in Example VI, the two preferred peptides disclosed in Example VI were injected into rabbits. Both peptides were conjugated to a carrier protein, KLH, and emulsified in incomplete Freund's adjuvant. The rabbits were boosted after 1 month and bled. Antibody levels in sera were tested by enzyme linked immunosorebant assay (ELISA) using unconjugated peptides. The ELISA revealed that the immunized animals generated high levels of antibodies to the peptides.

ELISA was also performed on plates coated with partially purified type IIA procollagen and partially purified type IIA propeptide isolated from culture media from human chondrocytes. (Data not shown.) Western blotting confirmed that the antibody is specific for type IIA procollagens containing the N-propeptide. In addition, tissue sections stained positively by immunohistochemistry using the antisera.

Alternatively, the presence of type IIA procollagen or propeptide in a fluid sample (e.g., serum, urine or synovial fluid) can be determined by immunoassay using anti-type IIA peptide domain antibod(ies).

Example VIII

DNA Sequence of Col2A1

The complete DNA sequence of the 5' portion of the human type II procollagen gene (Col2A1) has been determined. The DNA sequence for the human alpha-1 collagen type II gene, exons 1, 2 and 3, has been submitted to GenBank, and has been accorded Accession Number M60299. Also see Ryan, M. C. et al., (1990) *Genomics* 8:41–48.

Although the present invention has been described in considerable detail with reference to certain preferred versions thereof, other versions for identifying type IIA mRNA and/or type IIA procollagen/propeptide in samples from non-embryonic humans are possible. Therefore, the spirit and scope of the appended claims should not be limited to the description of the preferred versions contained therein.

I claim:

1. A method for determining cartilage synthesis associated with osteoarthritis in a non-embryonic human subject comprising detecting the presence of collagen type IIA propeptide or collagen type IIA in a tissue or fluid sample from said human subject wherein detected collagen type IIA propeptide or collagen type IIA procollagen indicates cartilage synthesis associated with osteoarthritis.

2. A method according to claim 1 wherein said type IIA procollagen or type IIA procollagen are detected by means of immunoassays, immunohistochemical techniques, or by sequencing.

3. A method according to claim 1 wherein the tissue sample is an articular cartilage tissue sample.

4. A method according to claim 1 wherein the sample is serum, urine or synovial joint fluid.

5. An immunoassay for detecting amino-terminal procollagen or propeptide type IIA in a fluid or tissue sample from a non-embryonic individual comprising (1) immunizing an animal with antigenic peptide encoded by exon 2 of the human pro-α1(II) gene, (2) recovering antibodies from the serum of animals immunized in step (1), (3) contacting the fluid or tissue sample from the non-embryonic individual with antibod(ies) from step (2), and (4) determining the presence of amino-terminal procollagen or propeptide type IIA in the fluid or tissue sample from the presence of antibody-antigen complex.

6. A method according to claim 5 wherein said antibodies contain at least one antibody to the peptide sequences consisting of Cys-Glu-Asp-Val-Lys-Asp (SEQ ID. NO.:3) and Cys-Pro-Thr-Asp-Leu-Ala-Thr-Ala-Ser-Gly (SEQ ID. NO.:4).

7. A method according to claim 5 wherein said sample is a tissue sample from articular cartilage or a fluid sample consisting of serum, synovial fluid or urine.

8. A method for determining the presence of type IIA procollagen or propeptide in serum, synovial fluid, or urine from an individual with osteoarthritis comprising contacting a serum, synovial fluid or urine sample from said individual with antisera to antigenic peptide encoded by exon 2 of the human pro-α1(II) gene, and determining the presence of an antibody-antigen complex.

9. A method according to claim 8 wherein said antibodies contain at least one antibody to the peptide sequences consisting of Cys-Glu-Asp-Val-Lys-Asp (SEQ ID. NO.: 3) Cys-Pro-Thr-Asp-Leu-Ala-Thr-Ala-Ser-Gly (SEQ ID. NO.: 4).

10. An immunohistochemical method for determining the presence of type IIA procollagen or propeptide in human articular cartilage from a non-embryonic individual comprising contacting a human articular cartilage tissue sample with antibod(ies) to antigenic peptide encoded by exon 2 of the human pro-α1(II) gene, wherein the presence of an antibody-antigen complex determines the presence of type IIA procollagen or propeptide in the human articular cartilage sample.

11. A method according to claim 10 wherein said antibodies are antibodies to at least one of the following peptide sequences: (1) Cys-Glu-Asp-Val-Lys-Asp (SEQ ID NO.: 3); (2) Cys-Pro-Thr-Asp-Leu-Ala-Thr-Ala-Ser-Gly (SEQ ID NO.: 4).

* * * * *

UNITED STATES PATENT AND TRADEMARK OFFICE
CERTIFICATE OF CORRECTION

PATENT NO. : 5,780,240      Page 1 of 4
DATED : July 14, 1998
INVENTOR(S) : Linda J. Sandell It is certified that error appears in the above-indentified patent and that said Letters Patent is hereby corrected as shown below:

Cover page, Title, after "PROCOLLAGEN/PROPEPTIDE" insert --OR TYPE IIA MRNA--

At Column 1, line 34, the term "e.g." should be italicized to read --*e.g.*--.
At Column 1, line 60, the term "et al." should be italicized to read --*et al.*--.
At Column 2, line 2-3, the term "et al." should be italicized and a period should be added to read --*et al.*--.
At Column 2, line 11, the term "et al." should be italicized and a period should be added to read --*et al.*--.
At Column 2, line 32, the term "i.e." should be italicized to read --*i.e.*--.
At Column 2, line 48, the term "in situ" should be italicized to read --*in situ*--.
At Column 2, line 49, the word "identifies" should read --identified--.
At Column 2, line 58, the term "i.e." should be italicized to read --*i.e.*--.
At Column 2, line 59, the term "e.g." should be italicized to read --*e.g.*--.
At Column 2, line 62, the term "e.g." should be italicized to read --*e.g.*--.
At Column 3, line 1, the term "e.g." should be italicized to read --*e.g.*--, and the term "etc." should be italicized to read --*etc.*--.
At Column 3, line 8, the term "e.g." should be italicized to read --*e.g.*--.
At Column 3, line 17, the term "e.g." should be italicized to read --*e.g.*--.
At Column 3, line 21, the term "i.e." should be italicized to read --*i.e.*--.
At Column 3, line 22, the term "e.g." should be italicized to read --*e.g.*--.
At Column 3, line 24-25, the term "in situ" should be italicized to read --*in situ*--.
At Column 3, line 48, the term "e.g." should be italicized to read --*e.g.*--.
At Column 3, line 59, the term "in situ" should be italicized to read --*in situ*--.
At Column 3, line 64, the term "in situ" should be italicized to read --*in situ*--.
At Column 4, line 37, the term "In Situ" should be italicized to read --*In Situ*--.
At Column 4, line 39, the term "in situ" should be italicized to read --*in situ*--.

UNITED STATES PATENT AND TRADEMARK OFFICE
CERTIFICATE OF CORRECTION

PATENT NO. : 5,780,240
DATED : July 14, 1998
INVENTOR(S) : Linda J. Sandell

Page 2 of 4

It is certified that error appears in the above-indentified patent and that said Letters Patent is hereby corrected as shown below:

At Column 4, line 43, the term "in situ" should be italicized to read --*in situ*--.
At Column 4, line 44, the term "in situ" should be italicized to read --*in situ*--.
At Column 4, line 45, the term "et al." should be italicized and a period should be added to read --*et al.*--.
At Column 5, line 1, the word "Eastmen" should read --Eastman--.
Col. 5, line 46, "3 mg/ml" should read --(3mg/ml--.
At Column 6, line 3, the term "e.g." should be italicized to read --*e.g.*--.
At Column 6, line 5, the term "e.g." should be italicized to read --*e.g.*--.
At Column 6, line 9, the term "NaCI" should read --NaCl--.
At Column 6, line 24, the term "in situ" should be italicized to read --*in situ*--.
At Column 6, line 45, the term "In situ" should be italicized to read --*In situ*--.
At Column 6, line 57, the term "Kpn-HincII" should read --*Kpn-HincII*--.
At Column 6, line 58, the term "in vitro" should be italicized to read --*in vitro*--.
At Column 7, line 18-19, the term "et al." should be italicized to read --*et al.*--, and the term "*Articular Cartilage and Osteoarthritis*", should not be italicized but should be underlined to read --<u>Articular Cartilage and Osteoarthritis</u>--.
At Column 8, line 5, the word "is" should read --are--.
At Column 8, line 30, the term "e.g." should be italicized to read --*e.g.*--.
At Column 8, line 43, the term "et al." should be italicized to read --*et al.*--.

UNITED STATES PATENT AND TRADEMARK OFFICE
CERTIFICATE OF CORRECTION

PATENT NO. : 5,780,240  Page 3 of 4
DATED : July 14, 1998
INVENTOR(S) : Linda J. Sandell It is certified that error appears in the above-indentified patent and that said Letters Patent is hereby corrected as shown below:

In the Sequence Listing table following Column 8, following the sequence under Roman Numeral (xi) SEQUENCE DESCRIPTION: SEQ ID NO: 1:, the number "24" should be moved so as to be under the second instance of sequence letters "GC" in the first part of the sequence ("TGCCAGCCTC"):
--TGCCAGCCTC CTGGACATCC TGGC
            24--.

In the Sequence Listing table following Column 8, following the sequence under Roman Numeral (xi), SEQUENCE DESCRIPTION: SEQ ID NO: 2:, the number "24" should be moved so as to be under the sequence letters "GG" in the first part of the sequence ("CTCCTGGTTG"):
--CTCCTGGTTG CCGGACATCC TGGC
            24--.

UNITED STATES PATENT AND TRADEMARK OFFICE
CERTIFICATE OF CORRECTION

PATENT NO.   : 5,780,240
DATED        : July 14, 1998
INVENTOR(S)  : Linda J. Sandell It is certified that error appears in the above-indentified patent and that said Letters Patent is hereby corrected as shown below:

In Claim 1, Line 4, (Column 9, Line 50), after "type IIA", insert --procollagen--.

In Claim 2, Line 2, (Column 9, line 55), delete the first instance of the word "procollagen", and insert --propeptide--.

In Claim 9, Line 4, (Column 11, line 1-2), between "(SEQ ID. NO.: 3)" and "Cys", insert the word --and--.

Signed and Sealed this

First Day of December, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,780,240

DATED : July 14, 1998

INVENTOR(S) : Linda J. Sandell

It is certified that error appears in the above-identified patent and that said Letters Patent is hereby corrected as shown below:

Column 6, line 11, change "h" to --hours--.

Signed and Sealed this

Second Day of March, 1999

*Attest:*

*Attesting Officer*

Q. TODD DICKINSON

*Acting Commissioner of Patents and Trademarks*